(12) United States Patent
Kurihara

(10) Patent No.: US 9,040,769 B2
(45) Date of Patent: May 26, 2015

(54) ABSORBENT ARTICLE

(75) Inventor: Ryoko Kurihara, Sakura (JP)

(73) Assignee: DAIO Paper Corporation, Ehime (JP)

( * ) Notice: Subject to any disclaimer, the term of this patent is extended or adjusted under 35 U.S.C. 154(b) by 115 days.

(21) Appl. No.: 13/820,007

(22) PCT Filed: Aug. 31, 2011

(86) PCT No.: PCT/JP2011/069772
§ 371 (c)(1),
(2), (4) Date: Feb. 28, 2013

(87) PCT Pub. No.: WO2012/029851
PCT Pub. Date: Mar. 8, 2012

(65) Prior Publication Data
US 2013/0165885 A1 Jun. 27, 2013

(30) Foreign Application Priority Data
Aug. 31, 2010 (JP) .................. 2010-193608

(51) Int. Cl.
*A61F 13/533* (2006.01)
*A61F 13/538* (2006.01)
*A61F 13/475* (2006.01)
*A61F 13/472* (2006.01)

(52) U.S. Cl.
CPC ........... *A61F 13/538* (2013.01); *A61F 13/4756* (2013.01); *A61F 2013/47281* (2013.01); *A61F 13/533* (2013.01)

(58) Field of Classification Search
CPC .............. A61F 13/4756; A61F 13/533; A61F 2013/53778; A61F 2013/53782; A61F 2013/530875
See application file for complete search history.

(56) References Cited

U.S. PATENT DOCUMENTS

| 5,653,842 | A | 8/1997 | Kuen | |
|---|---|---|---|---|
| 2002/0143311 | A1* | 10/2002 | Brisebois | 604/385.01 |
| 2002/0156450 | A1* | 10/2002 | Drevik et al. | 604/385.101 |
| 2003/0120235 | A1* | 6/2003 | Boulanger | 604/378 |
| 2003/0225385 | A1* | 12/2003 | Glaug et al. | 604/385.01 |
| 2004/0015145 | A1* | 1/2004 | Miura et al. | 604/367 |
| 2005/0182374 | A1* | 8/2005 | Zander et al. | 604/380 |
| 2006/0069371 | A1* | 3/2006 | Ohashi et al. | 604/385.01 |
| 2006/0100598 | A1* | 5/2006 | Tamura et al. | 604/380 |
| 2006/0122569 | A1* | 6/2006 | Drevik et al. | 604/360 |
| 2006/0276767 | A1* | 12/2006 | Ueminami et al. | 604/385.31 |
| 2008/0021427 | A1* | 1/2008 | Iwao | 604/380 |
| 2009/0036854 | A1* | 2/2009 | Guidotti et al. | 604/369 |
| 2013/0131623 | A1* | 5/2013 | Kawakami | 604/380 |
| 2013/0211360 | A1* | 8/2013 | Hashino et al. | 604/380 |
| 2014/0163511 | A1* | 6/2014 | Roe et al. | 604/385.101 |

FOREIGN PATENT DOCUMENTS

| JP | 59-130724 | 9/1984 |
|---|---|---|
| JP | 6-39000 | 2/1994 |

(Continued)

*Primary Examiner* — Susan Su
(74) *Attorney, Agent, or Firm* — Jordan and Hamburg LLP

(57) ABSTRACT

An absorbent article, such as a sanitary napkin and the like, constituted of an absorbing body between permeable (skin contact surface) and impermeable (skin non-contact surface) sheets, is provided with intermittent recess grooves formed in a longitudinal direction on the absorbent article on the skin non-contact surface side of the absorbing body, a plurality of laterally elongated peripheral embosses formed at intervals in the longitudinal direction of the absorbent article on absorbent body areas located peripherally to the recess grooves, and an absorbing body deficit portion formed at least between the recess grooves. Thus achieved are close contact with buttock cleavage and prevention of leakage to the rear.

9 Claims, 4 Drawing Sheets

(56) References Cited

FOREIGN PATENT DOCUMENTS

| | | |
|---|---|---|
| JP | 10-99372 | 4/1998 |
| JP | 2000-14022 | 1/2000 |
| JP | 2006-263205 | 10/2006 |
| JP | 3850103 | 11/2006 |
| JP | 4145289 | 9/2008 |

* cited by examiner

ABSORBENT ARTICLE

BACKGROUND OF THE INVENTION

The present invention relates to an absorbent article such as a sanitary napkin, a pantiliner, an incontinence pad and the like for absorbing menstrual blood, vaginal discharge and the like or more particularly to an absorbent article which improves close contact with a buttock cleavage and prevents leakage to the rear.

Hitherto, as absorbent articles such as a pantiliner, a sanitary napkin, a vaginal discharge sheet, an incontinence pad, toiletry products and the like, those interposing an absorbing body made of a cotton-state pulp between an impermeable back-surface sheet such as a polyethylene sheet, a polyethylene sheet-laminated unwoven cloth or the like and a permeable front-surface sheet such as a nonwoven cloth, a permeable plastic sheet or the like are known.

Many improvements have been made for this type of absorbent article, and in order to prevent leakage of body fluids, various means have been taken. Particularly, one of the factors of leakage in sanitary napkins overnight is leakage along the buttocks caused by a gap generated between the sanitary napkin and the buttock cleavage.

Thus, those formed so as to fit the buttock cleavage on the rear part have been developed. For example, Japanese Patent No. 3850103 discloses an absorbent article provided with a raised portion raised to the skin contact surface side on a rear part of an absorbing portion and a rear groove extending in the longitudinal direction of the absorbent article at the center in the width direction of the absorbent article on the skin non-contact surface side of the absorbing portion corresponding to the raised portion. Moreover, Japanese Patent No. 4145289 discloses an absorbent article in which a plurality of emboss grooves extending inward of an absorbing body from an upper surface of the absorbing body in the width direction of the absorbent article are formed, the absorbing body is high in the middle, and this high middle portion is formed of an upper layer and a lower layer.

SUMMARY OF INVENTION

In the absorbent article described in Japanese Patent No. 3850103, the rear part of the absorbing portion is deformed into an inverted V-shape when a sanitary napkin is attached so that the sanitary napkin favorably fits the buttocks of a wearer by allowing the above-described rear grooves to function as a flexible shaft.

Though deformation performance in the transverse surface direction is improved by forming the above-described rear grooves functioning as the flexible shaft, since the above-described rear groove is formed as a linear recess groove compressed at a high density, deformation performance in the longitudinal direction of the absorbent article, that is, the deformation performance with the transverse direction as the shaft deteriorates to the contrary. As a result, deformation of the napkin rear part along the roundness of the buttocks becomes difficult, and a gap is generated between the napkin and the buttocks, which might cause leakage to the rear.

On the other hand, in the absorbent article described in Japanese Patent No. 4145289, since a plurality of folding lines in the width direction are formed in the longitudinal direction of the absorbing body by forming the above-described emboss grooves, deformation performance of the absorbent article in the longitudinal direction is improved, the absorbent article becomes easily bendable and can be fit with the roundness of the buttocks in the front-and-rear direction. However, rigidity of the absorbing body in which the folding lines in the width direction are formed increases and close contact to the depth of the buttock cleavage becomes difficult, which might generate a thin gap between the absorbent article and the buttock cleavage and cause leakage to the rear.

Thus, the present invention has a main object to provide an absorbent article which improves close contact with the buttock cleavage and prevents leakage to the rear.

In order to solve the above-described problems, according to a first aspect of the present invention an absorbent article is provided in which an absorbing body is interposed between a permeable front-surface sheet and an impermeable back-surface sheet, characterized in that intermittent recess grooves are formed in a longitudinal direction of the above-described absorbent article on the skin non-contact surface side of the above-described absorbing body, a plurality of laterally long peripheral embosses are formed at intervals in the longitudinal direction of the absorbent article on the absorbing body located in the periphery of the above-described recess groove, and an absorbing-body deficit portion is formed at least between the above-described recess grooves.

By forming the intermittent recess grooves in the longitudinal direction of the absorbent article on the skin non-contact surface side of the absorbing body, a shaft portion along the formed row of the above-described recess grooves is made thinner than the other portions and thus the rigidity (sectional secondary moment) lowers. Therefore, deformation performance to be raised along the buttock cleavage in the transverse direction of the absorbent article (width direction of the absorbent article) can be ensured by the flexible shaft (longitudinal flexible shaft) with the formed row of the recess grooves as a shaft. Furthermore, by forming a plurality of the laterally long peripheral embosses at intervals in the longitudinal direction of the above-described absorbent article on the absorbing body located in the periphery of the above-described recess groove, resistance is given to the absorbing body in the periphery of the recess groove against bending force in transverse surface direction of the absorbent article, rigidity difference is given between the absorbing body in the vicinity of the recess groove and the absorbing body in the periphery thereof, and deformation performance to deform only the center part along the buttock cleavage is ensured.

Moreover, by forming the absorbing body deficit portion at least between the above-described recess grooves, if the raised portion along the buttock cleavage is curved along the roundness in the front-and-rear direction of the buttocks, deformation in a compression direction or a tension direction of the absorbing body is absorbed by the above-described absorbing-body deficit portion, generation of wrinkles in the width direction becomes less likely on the skin contact surface side, and favorable close contact up to the depth in the thin buttock cleavage can be realized.

Therefore, the center part in the width direction in the rear can be easily raised in the longitudinal direction and this raised portion can be easily curved along the roundness in the front-and-rear direction of the buttocks and thus, close contact with the buttock cleavage is improved, and leakage to the rear can be prevented.

In a second aspect of the present invention, the absorbent article of the first aspect is provided in which an absorbing body middle high portion extending in the longitudinal direction of the above-described absorbent article and raised to the skin contact surface side is provided at least on the center part in the rear of the above-described absorbent article, intermittent recess grooves are formed in the longitudinal direction of the above-described absorbent article on the skin non-contact surface side of the absorbing body corresponding to the above-described absorbing-body middle high portion, a plurality of laterally long peripheral embosses are formed at intervals in the longitudinal direction of the above-described absorbent article on the absorbing body located in the periphery of the above-described absorbing-body middle high portion, and an absorbing-body deficit portion is formed at least between the above-described recess grooves of the absorbing body corresponding to the above-described absorbing-body middle high portion.

The second aspect of the invention is a configuration in which is provided an absorbing-body middle high portion extending in the longitudinal direction of the above-described absorbent article and raised to the skin contact surface side at least on the center part in the rear of the above-described absorbent article.

In a third aspect of the present invention, the absorbent article of the first or second aspect is provided in which a pair of right and left rear portion embosses are formed in the substantially longitudinal direction of the above-described absorbent article on the skin contact surface side of the above-described absorbing body in a region corresponding to the buttocks of a wearer, and a fit emboss extending to the center part side in the width direction of the above-described absorbent article from the above-described rear portion emboss is formed at a position corresponding to the above-described absorbing-body deficit portion.

In the third aspect of the invention, since the pair of right and left rear portion embosses are formed in the substantially longitudinal direction of the above-described absorbent article on the skin contact surface side of the above-described absorbing body in the region corresponding to the buttocks of a wearer, and the fit emboss extending to the center part side in the width direction of the above-described absorbent article from the above-described rear portion emboss is formed at the position corresponding to the above-described absorbing-body deficit portion, the absorbent article can be reliably curved along the roundness in the front-and-rear direction of the buttocks at the formation position of the absorbing-body deficit portion by using the above-described fit emboss as a base point.

In a fourth aspect of the invention, the absorbent article of any of the first to third aspects of the invention is provided in which the above-described absorbing-body deficit portion has any of rectangular, diamond, wedge or triangular shape.

In the fourth aspect of the invention the invention, a specific examples of a plan shape of the absorbing-body deficit portion are rectangular, diamond, wedge or triangular shape.

In a fifth aspect of the invention, the absorbent article of any of the first to fourth aspects of the invention is provided in which the above-described absorbing-body deficit portion has a three-dimensional shape in which the shape is changed in the thickness direction of the absorbing body.

In the fifth aspect of the invention, since the absorbing-body deficit portion is formed to have a three-dimensional shape in which the shape is changed in the thickness direction of the absorbing body, if the absorbent article is curved along the roundness in the front-and-rear direction of the buttocks, deformation in which the skin contact surface side is compressed, while the skin non-contact surface side is tensioned can be absorbed as appropriate.

As described above in detail, according to the present invention, an absorbent article which improves close contact with the buttock cleavage and prevents leakage to the rear is provided.

An embodiment of the present invention will be described below in detail by referring to the attached drawings.

DETAILED DESCRIPTION OF THE INVENTION

Basic Structure of Sanitary Napkin 1

Figure 1:
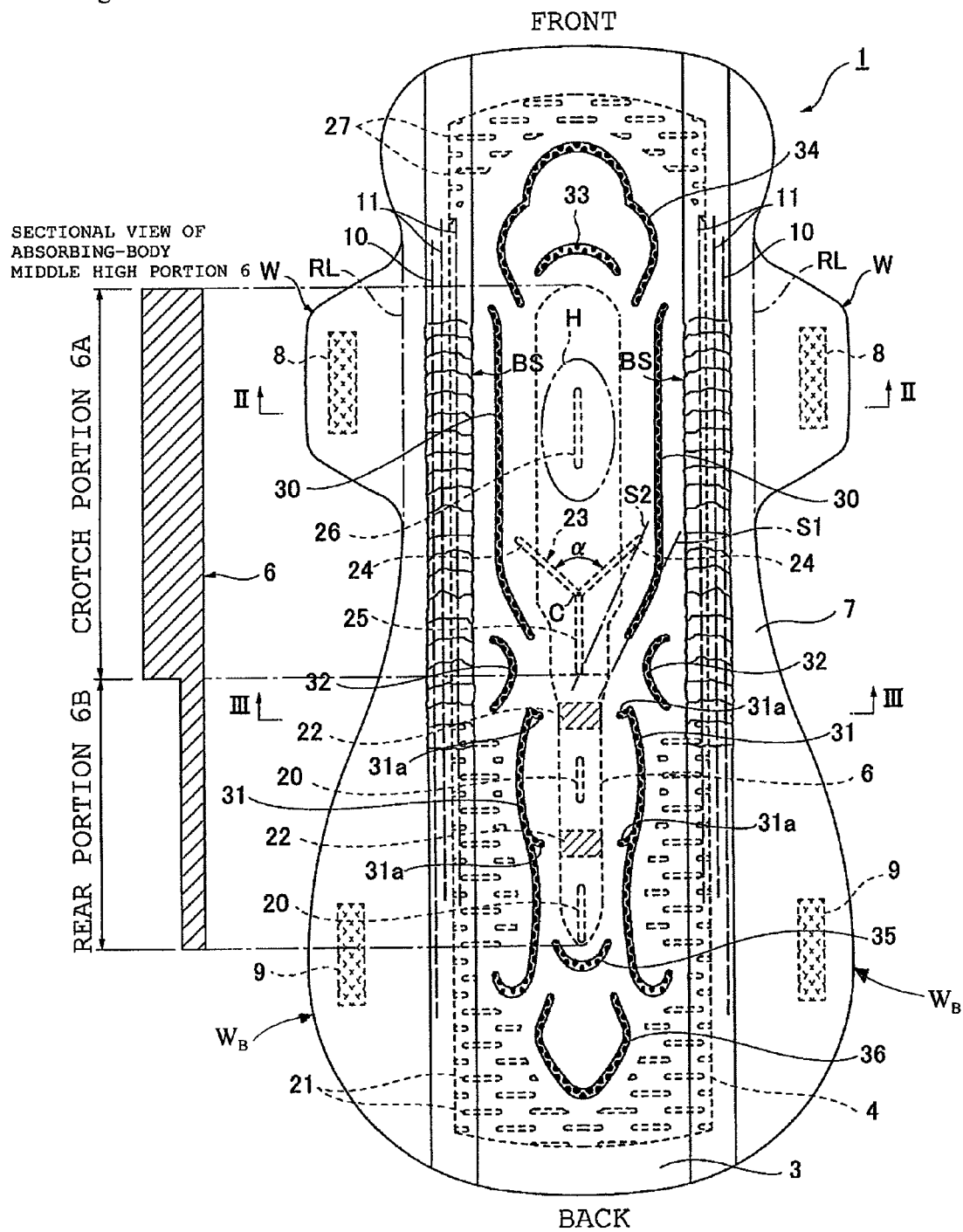
FIG. 1 is an extended diagram of a sanitary napkin 1 according to the present invention.
Figure 2:
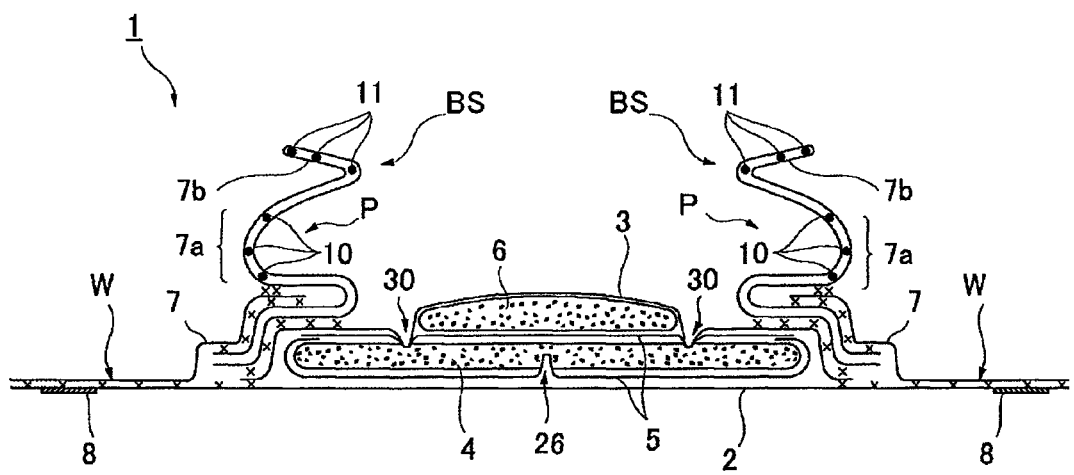
FIG. 2 is a sectional view taken on FIG. 1 line II-II in the direction shown by the line II-II arrows.
Figure 3:
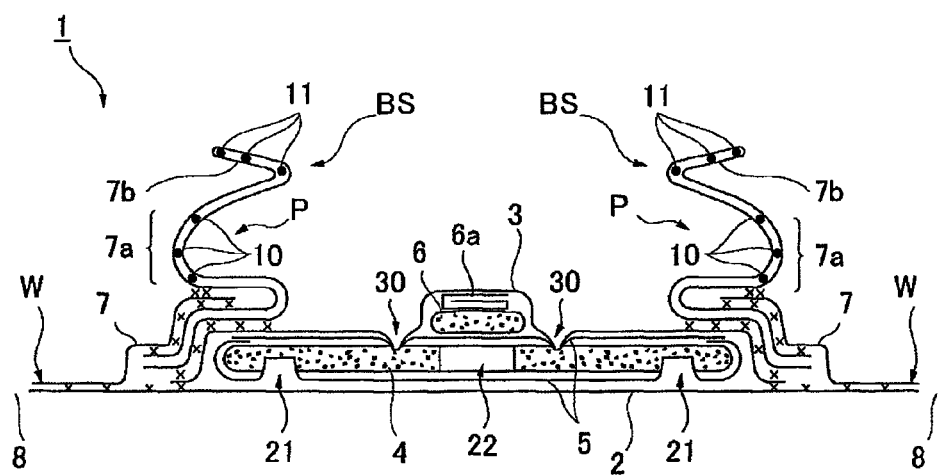
FIG. 3 is a sectional view taken on FIG. 1 line III-III in the direction shown by the line III-III arrows.
Figure 4:
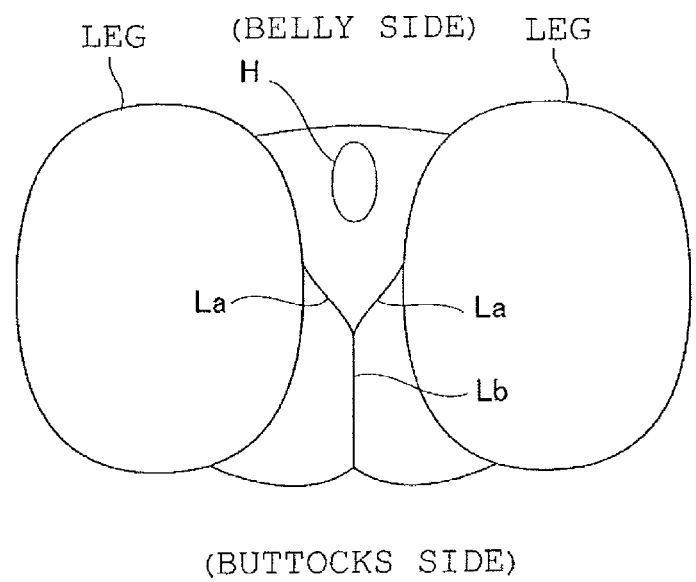
FIG. 4 is a lower face view of a human body illustrating a crotch portion structure.
Figure 5A:
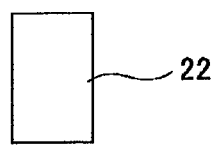
FIG. 5 is a plan view of an absorbing-body deficit portion 22.
Figure 5C:
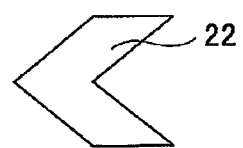
Figure 5B:
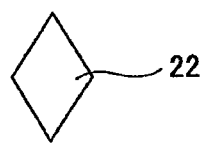
Figure 5D:
Figure 6A:
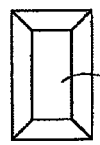
FIG. 6 are a plan view and a sectional view of the absorbing-body deficit portion 22 according to other mode.
Figure 6A:
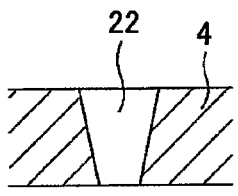
Figure 6B:
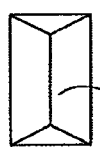
Figure 6B:
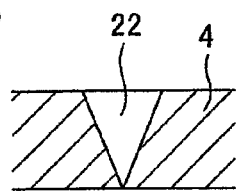

A sanitary napkin 1 according to the present invention is, as illustrated in FIGS. 1 to 3, mainly composed of an impermeable back sheet 2 made of a polyethylene sheet or the like, a permeable top sheet 3 which allows menstrual blood, vaginal discharge and the like to pass rapidly, absorbing bodies 4 and 6, each made of cotton-state pulp or synthetic pulp or the like interposed between the sheets 2 and 3, an encapsulating sheet 5 surrounding the above-described absorbing body 4 for maintaining the shape of this absorbing body 4 and for improving diffusion performance, and a pair of right and left three-dimensional gatherings BS and BS provided protruding to the surface side within a predetermined section in the front-and-rear direction so as to include at least a body fluid discharge portion using a substantially side edge portion of the above-described absorbing body 4 as a standing base end, in which, in the periphery of the above-described absorbing body 4, outer edge portions of the above-described impermeable back sheet 2 and the permeable top sheet 3 are bonded together by an adhesive such as hot-melt or bonding means such as a heat seal or the like in the upper- and lower-end edge portions, while in the both-side edge portions, the above-described impermeable back sheet 2 extending closer to the side than the absorbing body 4 and a side unwoven cloth 7 forming the above-described three-dimensional gathering BS are bonded together by an adhesive such as hot-melt or bonding means such as a heat seal or the like to form a laminated sheet portion constituted of the impermeable back sheet 2 and the side unwoven cloth 7 laminated together so that wing-shaped flaps W and W protruding to the sides are formed by that laminated sheet portion and second wing-shaped flaps $W_B$ and $W_B$ are formed on portions located closer to the buttocks side than flaps W and W.

The structure of the above-described sanitary napkin 1 will be further described below in detail.

The above-described impermeable back sheet 2 uses a sheet material having at least water shielding property such as polyethylene or the like, but those having moisture permeability tend to be used from the viewpoint of prevention of damp feeling in recent years. As this water-shielding/moisture permeable sheet material, a micro-porous sheet obtained by melting and kneading inorganic filler in an olefin resin such as polyethylene, polypropylene and the like and molding a sheet and then, by drawing it in an uniaxial or biaxial direction is used favorably. On the non-use surface side (outer surface) of the above-described impermeable back sheet 2, one or a plurality of adhesive layers (not shown) are formed so that the sanitary napkin 1 is fixed to an underwear when the napkin is to be attached to the body. As the impermeable back sheet 2, a poly-laminated unwoven cloth obtained by laminating a plastic film and an unwoven cloth may be used.

Subsequently, for the above-described permeable top sheet 3, a porous or non-porous unwoven cloth or a porous plastic sheet or the like is suitably used. As material fibers constituting the unwoven cloth, in addition to synthetic fibers including olefins such as polyethylene, polypropylene and the like and polyesters, polyamide and the like, recycled fibers such as rayon, cupra and the like, and natural fibers such as cotton and the like can be used, and unwoven cloth obtained by appropriate processing methods such as spunrace method, spun-bond method, thermal bond method, melt-blown method, needle punch method and the like can be used. Among these processing methods, the spunrace method is excellent in its rich flexibility and drape property, while the thermal bond method is excellent in bulkiness and softness. If a large number of through holes are formed in the above-described permeable top sheet 3, menstrual blood, vaginal discharge and the like (hereinafter collectively referred to as body fluids.) can be absorbed more rapidly, and dry touch feeling becomes excellent.

As the above-described absorbing body 4, it is only necessary that it can absorb/maintain body fluids, and those obtained by mixing water-absorbing polymer powders in fluff-state pulp are suitably used in view of the absorbing function and price. The above-described absorbing body 4 is preferably surrounded by the encapsulating sheet 5 for maintaining the shape or the like. As the above-described encapsulating sheet 5, crepe paper, hydrophilic unwoven cloth and the like can be used.

In the above-described absorbing body 4 and/or an absorbing-body middle high portion 6 which will be described later, synthetic fibers may be mixed. As the above-described synthetic fibers, for example, polyolefin such as polyethylene, polypropylene or the like, polyester such as polyethylene terephthalate, polybutylene terephthalate or the like, polyamide such as nylon, and their copolymers and the like can be used, and two kinds of them may be mixed. Moreover, composite fibers such as core-and-sheath fibers using fibers with a high melting point as a core and fibers with a low melting point as a sheath, side-by-side fibers, split fibers and the like can be also used. The above-described synthetic fibers are preferably used after being surface treated by hydrophilic treatment agent in the case of hydrophobic fibers so as to give affinity to the body fluids.

On the used surface side of the above-described absorbing body 4, the absorbing-body middle high portion 6 elongated in the napkin longitudinal direction on the center part in the width direction, extending in the longitudinal direction and raised to the skin contact surface side may be formed. This absorbing-body middle high portion 6 is formed in the elongated manner on the center part in the width direction from a crotch portion 6A including a blood discharge opening portion H of a wearer and also including a portion corresponding to a Y-shaped groove 23 which will be described later to a rear portion 6B continuing from the rear end of this crotch portion 6A. In the above-described absorbing-body middle high portion 6, the crotch portion 6A is preferably provided having a predetermined height in order to maintain an absorbing amount and close contact with a blood discharge opening, but the rear portion 6B is preferably formed thinner than the above-described crotch portion 6A or is not formed so as not to obstruct deformation by the emboss which will be described later. The thickness of the above-described absorbing-body middle high portion 6 is 3 to 20 mm or preferably 5 to 15 mm for the crotch portion 6A, and the rear portion 6B has thickness of 0 to 10 mm or preferably 0 to 3 mm. Moreover, in order not to have a wearer feel insecure by thinning or eliminating the absorbing-body middle high portion 6 of the above-described rear portion 6B, a bulky second sheet 6a may be disposed on the skin contact surface side of this rear portion 6B as illustrated in FIG. 3. This second sheet 6a preferably uses a material with high cushion performance to such a degree that does not affect deformation of the absorbing bodies 4 and 6. Moreover, the above-described absorbing-body middle high portion 6 is formed such that the rear portion 6B is narrower than the front portion 6A and such that the width and/or the thickness gradually reduces toward the rear on the boundary between the front portion 6A and the rear portion 6B. The boundary range in which the width and/or the thickness gradually reduces preferably has a start position on the front side which is somewhat on the rear side of a portion corresponding to an intersection C of the Y-shaped groove 23 which will be described in detail later and an end position on the rear side which is somewhat on the rear side of a portion corresponding to the rear end of a rear groove 25 of the Y-shaped groove 23 which will be described in detail later. As a result, fitting performance of the boundary portion between the crotch portion 6A and the rear portion 6B is improved.

On the other hand, the width dimension of the above-described permeable top sheet 3 in the illustrated example is, as illustrated in the cross sectional views in FIGS. 2 and 3, somewhat longer than the width of the absorbing body 4 and only covers the absorbing bodies 4 and 6 and the above-described three-dimensional gathering BS is configured by using a side unwoven cloth 7 separate from the above-described permeable top sheet 3 or specifically, an unwoven fabric material subjected to appropriate water repellent treatment or hydrophilic treatment in accordance with its purpose of preventing permeation of menstrual blood, vaginal discharge and the like or of improving skin touch feeling. As such side unwoven cloth 7, those formed by using natural fibers, synthetic fibers or recycled fibers as a material and using an appropriate forming method can be used, but in order to eliminate rough feeling and to prevent damp feeling, an unwoven cloth with suppressed weight per unit area and having air permeability is preferably used. Specifically, an unwoven cloth fabricated with a weight per unit area of 13 to 23 $g/m^2$ is preferably used, and an unwoven cloth subjected to water repellent treatment and coated with silicon, paraffin, alkyl chromic chloride water repellent agent and the like in order to reliably prevent permeation of body fluids is suitably used.

In the above-described side unwoven cloth 7, as illustrated in FIGS. 2 and 3, an outer portion from an intermediate portion in the width direction is bonded by an adhesive such as hot melt over a range from an inward position of the absorbing body 4 to the outer edge of the impermeable back sheet 2 somewhat beyond the side edge of the absorbing body so that the pair of right and left wing flaps W and W are formed at side portion positions of the absorbing body substantially corresponding to the body fluid discharge portion by a laminated sheet portion of these above-described side unwoven cloth 7 and the impermeable back sheet 2, and the second wing-shaped flaps $W_B$ and $W_B$ are formed at the buttocks side positions by them. The outer surface sides of these wing-shaped flaps W and W and the second wing-shaped flaps $W_B$ and $W_B$ are provided with adhesive layers 8 . . . and 9 . . . , respectively, so that the above-described wing-shaped flaps W and W can be folded back to the opposite side at folding lines RL positions, rolled around the crotch portion of shorts and taped when being worn on the shorts.

On the other hand, the inner side portion of the above-described side unwoven cloth 7 is folded back substantially in double, an elastically extensible member which is an elastically extensible yarn, fixed at the both ends or at an appropriate position in the longitudinal direction in its intermediate portion in the height direction, is disposed inside the double sheet, and the three-dimensional gatherings BS and BS standing on the surface side are formed. Specifically, as illustrated in FIGS. 2 and 3, a side surface standing portion 7a standing from the side edge portion of the absorbing body 4 or its vicinity and a skin contact surface portion 7b having a predetermined width formed continuing from the distal end of this side surface standing portion 7a and substantially horizontally or with inclination toward the center side with respect to the surface of the napkin 1 are provided in the standing state, and the above-described side surface standing portion 7a is located outside from the outer side end edge of the above-described skin contact surface portion 7b. In the above-described side surface standing portion 7a and the skin contact surface portion 7b, one or a plurality of or three each in the illustrated example of the elastically extensible members (yarns) 10 . . . and 11 . . . are disposed in the longitudinal direction of the sanitary napkin 1, respectively.

[Structure of Embosses and the Like]

Subsequently, structures of the absorbing-body deficit portion in which the emboss and the absorbing body is given a deficit formed on the skin non-contact surface side and the emboss formed on the skin contact surface side will be described below.

<Emboss and Absorbing-Body Deficit Portion Formed on the Skin Non-Contact Surface Side>

In this sanitary napkin 1, as illustrated in FIGS. 1 to 3, intermittent recess grooves 20, 20 . . . are formed in the longitudinal direction of the above-described sanitary napkin 1 on the skin non-contact surface side of the above-described absorbing body 4. That is, in this sanitary napkin 1, the recess groove is not formed continuously, but the intermittent recess grooves 20, 20 . . . in which a relatively short and linear recess emboss and a non-emboss portion alternately form a row are formed so as to ensure deformation performance in the transverse direction by using the napkin longitudinal axis along the above-described recess grooves 20, 20 as a flexible shaft. The above-described recess groove 20 is formed at two spots each in the front and rear in the illustrated example, but it may be formed at three or more positions.

Moreover, a plurality of laterally long peripheral embosses 21, 21 . . . at intervals in the longitudinal direction of the above-described sanitary napkin 1 are formed on the skin non-contact surface side of the absorbing body 4 located in the periphery of the above-described recess grooves 20 and 20. By forming the above-described peripheral embosses 21, resistance against bending in the napkin transverse surface direction (napkin width direction) is given to the periphery of the recess groove 20, that is, to the absorbing body 4 except the center part in the width direction in the rear part of the sanitary napkin 1, a rigidity difference in the napkin transverse surface direction is generated between the absorbing body 4 in the vicinity of the recess groove 20 and the absorbing body 4 in the periphery, and only the absorbing body 4 in the center part in the width direction can be deformed along the buttock cleavage.

Moreover, in the sanitary napkin 1, the absorbing-body deficit portion 22 in which the absorbing body 4 is given a deficit is formed at least between the above-described recess grooves 20 and 20, that is, in the non-emboss portion of the above-described recess groove 20. In the illustrated example, in addition to that between the recess grooves 20 and 20, the absorbing-body deficit portion is provided also between the Y-shaped groove 23 which will be described later and the recess groove 20. In a case in which the center part in the width direction is raised by using the formed row of the recess grooves 20 and 20 as a flexible shaft as described above and this raised portion is curved along the roundness in the front-and-rear direction of the buttocks, deformation in the compression direction or the tension direction of the absorbing body 4 is absorbed by the above-described absorbing-body deficit portion 22, generation of wrinkles in the width direction becomes less likely on the skin contact surface side, and favorable close contact up to the depth in the thin buttock cleavage is realized.

As described above, by means of the recess grooves 20, the periphery emboss 21, and the absorbing-body deficit portion 22 formed on the skin non-contact surface side of the absorbing body 4, the center part in the width direction in the rear of the sanitary napkin 1 can be easily raised in the napkin longitudinal direction and this raised portion can be easily curved along the roundness in the front-and-rear direction of the buttocks and thus, close contact with the buttock cleavage is improved, and leakage of the body fluids to the rear can be prevented.

On the other hand, on the skin non-contact surface side of the above-described absorbing body 4, the Y-shaped groove 23 formed of the pair of right and left front grooves 24 and 24 formed toward the both sides diagonally front from the intersection C in the center part in the width direction closer to the rear than the blood discharge opening portion H and the rear groove 25 formed toward the rear in the longitudinal direction of the sanitary napkin 1 from the above-described intersection C is formed. Since this Y-shaped groove 23 is formed, this Y-shaped groove 23 is made thinner than the other portions and rigidity (sectional secondary moment) lowers and thus, when the pressure of the legs on the both sides acts, a triangular pyramid raised portion having the above-described intersection C as an apex is formed by using this Y-shaped groove 23 as a flexible shaft. In this triangular pyramid-shaped raised portion, the lines extending to the both sides diagonally front made by the above-described front grooves 24 and 24 fit body lines La and La extending to the front both sides as a start portion of the buttock cleavage formed on the perineal portion from the rear part of the blood discharge opening portion H to the start portion of the buttock cleavage as a base point. Moreover, in the triangular pyramid-shaped raised portion, the line extending to the rear made by the rear groove 25 fits a line Lb of the buttock cleavage from the start portion of the buttock cleavage to the rear. Thus, the triangular pyramid-shaped raised portion formed by the Y-shaped groove 23 fits the shape of the body from the perineal portion to the rear from the blood discharge opening portion H to the buttock cleavage extremely favorably, and leakage of the body fluid along the buttocks to the rear can be prevented.

The structure of the above-described emboss and the like will be described in more detail. If the absorbing-body middle high portion 6 extending in the napkin longitudinal direction and raised to the skin contact surface side is formed at least on the center part in the rear of the sanitary napkin 1 as in the illustrated example, the above-described recess groove 20 is formed on the skin non-contact surface side of the absorbing body 4 corresponding to the above-described absorbing-body middle high portion 6, the above-described peripheral embosses 21 are formed in plural on the absorbing body 4 located in the periphery of the above-described absorbing-body middle high portion 6, and the above-described absorbing-body deficit portion 22 is formed at least between the above-described recess grooves 20 and 20 of the absorbing body 4 corresponding to the above-described absorbing-body middle high portion 6. Moreover, the above-described Y-shaped groove 23 is formed in the skin non-contact surface side of the absorbing body 4 corresponding to the above-described absorbing-body middle high portion 6 and its vicinity.

The depth of the above-described recess groove 20 is preferably formed so as to become at 30 to 95% of the thickness of the absorbing body 4 or preferably at 50 to 90%. If the depth of the recess groove 20 is less than 30%, not only deformation performance in the transverse direction but also the deformation performance in the longitudinal direction cannot be ensured. If the depth for the above-described recess groove 20 exceeds 95%, the recess groove 20 becomes too rigid and cannot be curved in the front-and-rear direction of the buttocks easily.

The length of the above-described recess groove 20 is preferably 5 to 30 mm or more preferably 10 to 20 mm. The length of each recess groove 20 does not have to be the same and in the illustrated example, the recess groove 20 on the rear side is formed longer than the one on the front side.

The above-described recess groove 20 is preferably produced in the absorbing body 4 before the encapsulating sheet 5 has been applied around the absorbing body 4 or produced in the absorbing body 4 together with the encapsulating sheet 5 surrounding the absorbing body 4.

The above-described peripheral emboss 21 is provided within a range outside of a rear-end design emboss 36, which will be described later, closer to the outer side than the pair of right and left rear portion embosses 31 and 31, which will be described later, in a region corresponding to the buttocks of the wearer in the illustrated example. In the above-described peripheral emboss 21, laterally long emboss grooves are aligned in a zigzag manner an plan view at intervals in the longitudinal direction of the sanitary napkin 1 and also at the intervals in the width direction.

The depth of the above-described peripheral emboss 21 is preferably 20 to 95% of the thickness of the absorbing body 4 or more preferably to 30 to 90%. As a result, a rigidity difference is given to the deformation in the width direction between the center part and the peripheral part and the center part can be reliably deformed. The length of the above-described peripheral emboss 21 is 5 to 20 mm or preferably 10 to 15 mm.

The above-described absorbing-body deficit portion 22 is formed within a range of 10 to 20 mm in the width direction of the sanitary napkin 1 and of 5 to 15 mm in the longitudinal direction, and as illustrated in FIG. 5, the absorbing body is given a deficit having (A) rectangular, (B) diamond, (C) and (D) wedge shapes and any other shapes including a triangular shape. Moreover, its sectional shape may be unchanging in configuration and dimensions in the thickness direction of the absorbing body but as illustrated in FIG. 6, the shape may change in the thickness direction of the absorbing body 4.

Since an angle between the body lines La and La formed on the perineal portion of an adult woman is relatively large, namely substantially 70° or greater, an angle α formed by the front grooves 24 and 24 of the above-described Y-shaped groove 23 is preferably 70° or greater and less than 180°, or more preferably 90° or greater and less than 150°, in order to have it fit with this body line. By setting the angle to 70° or greater, the rising effect of the absorbing body using the Y-shaped groove 23 as a flexible shaft is improved when a leg pressure is applied from the both sides.

The depth of the above-described Y-shaped groove 23 is preferably formed, similarly to the above-described recess groove 20, at 30 to 95% of the thickness of the absorbing body 4 or preferably 50 to 90%.

Moreover, the intersection C of the above-described Y-shaped groove 23 is set at least on the center part in the width direction of the sanitary napkin 1 and between 40 to 60 mm to the rear of the sanitary napkin 1 from the center of the blood discharge opening portion H in order to improve fitting performance with the perineal portion from the vaginal orifice to the vicinity of the anus on the rear side.

The above-described front grooves 24 and the rear groove 25 are formed each having the length of 20 mm to 40 mm from the above-described intersection C, respectively, and the lengths of the front grooves 24 and the rear groove 25 are preferably equal but they can be formed having different lengths.

Moreover, on the front side of the above-described Y-shaped groove 23 and on the skin non-contact surface side of the absorbing body 4 on the center part in the width direction of the sanitary napkin 1 corresponding to the blood discharge opening portion H, a linear emboss 26 is preferably formed in the longitudinal direction of the sanitary napkin 1. By forming this linear emboss 26, the center part in the width direction of the absorbing body 4 is raised in the longitudinal direction to the surface side using the linear emboss 26 as a flexible shaft, and the surface of the sanitary napkin 1 can be more reliably brought into close contact with the blood discharge opening portion of the wearer.

On the front end portion of the sanitary napkin 1, a plurality of laterally long front-end peripheral embosses 27, 27 . . . are formed at intervals in the longitudinal direction of the sanitary napkin 1. This improves resistance of the front end portion in the napkin width direction and prevents generation of wrinkles on the front end portion.

<Emboss Formed on Skin Contact Surface Side>

In this sanitary napkin 1, as illustrated in FIG. 1, the pair of right and left crotch portion embosses 30 and 30 are formed in substantially the longitudinal direction of the sanitary napkin 1 in a region corresponding to the crotch portion of the wearer on the skin contact surface side of the absorbing body 4, the pair of right and left rear portion embosses 31 and 31 are formed in a region corresponding to the buttocks of the wearer, and a pair of right and left intermediate portion embosses 32 are formed in an intermediate region between the crotch portion emboss 30 and the rear portion emboss 31 with a gap from the above-described embosses 30 and 31.

Moreover, a front-end umbrella-shaped emboss 33 having a substantially umbrella shape is formed at the center part in the width direction of the sanitary napkin 1 on the front side of the above-described crotch portion emboss 30 (if the absorbing-body middle high portion 6 is provided as in the illustrated example, on the front side of the front end of this absorbing-body middle high portion 6), and a front-end design emboss 34 is formed so as to surround the region of the front side thereof. On the other hand, a rear portion of the above-described rear portion emboss 31 (if the absorbing-body middle high portion 6 is provided as in the illustrated example, on the rear side of the rear end of this absorbing-body middle high portion 6), a rear-end umbrella-shaped emboss 35 having a substantially umbrella shape is formed at the center part in the width direction of the sanitary napkin 1, and a rear-end design emboss 36 is formed on the further rear side with a gap.

The above-described crotch portion emboss 30 is formed as a pair of right and left embosses in the substantially longitudinal direction of the sanitary napkin 1 within a range including the blood discharge opening portion H with the rear end overlapping the start portion of the buttock cleavage. Its front end portion has a shape bent so as to slightly expand to the both sides and its inclination angle is formed as an angle substantially in parallel with the rear end portion of the above-described front-end design emboss 34.

Moreover, the rear end portion of the above-described crotch portion emboss 30 has a shape inclined to the center part in the width direction within a range having an overlapping margin in the width direction with the above-described Y-shaped groove 23, and its inclination angle is a predetermined inclination angle in view of a relationship with the above-described Y-shaped groove 23. Specifically, they are formed so that a virtual line S1 obtained by extending the inclined rear end portion of the crotch portion emboss 30 and a virtual line S2 connecting the front end of the front groove 24 of the above-described Y-shaped groove 23 and the rear end of the rear groove 25 become substantially in parallel with each other. The phrase "substantially in parallel" includes a case in which the inclination angle is formed within a range of an angle difference of ±5° in addition to a case in which the inclination angles of the virtual lines S1 and S2 with respect to the napkin longitudinal line fully coincide with each other.

By having the rear end portion of the above-described crotch portion emboss 30 at the inclination angle, the action direction of the leg pressure from the both sides can be converted by the rear end portion of this crotch portion emboss 30 to a direction orthogonal to the virtual line S2 connecting the front end of the front groove 24 and the rear end of the rear groove 25, and a region surrounded by the front groove 24 and the rear groove 25 of the Y-shaped groove 23 can be easily raised by the leg pressure from the both sides.

The above-described rear portion emboss 31 is formed as a pair of right and left embosses in the substantially longitudinal direction of the sanitary napkin 1 within a range corresponding to the buttock cleavage for firmly raising the center part in the width direction of the absorbing body on the rear portion along the buttock cleavage. The rear portion emboss 31 has the substantially front half formed by a curve expanded to the outside and the remaining rear side formed by a curve expanded to the inside. Moreover, its rear end portion is formed having a shape bent in a semi-arc state toward the outside.

Moreover, in the above-described rear portion emboss 31, fit embosses 31a, 31a . . . extending from the rear portion emboss 31 to the center side in the napkin width direction are formed at positions corresponding to the above-described absorbing-body deficit portion 22. As a result, the sanitary napkin can be reliably curved along the roundness in the front-and-rear direction of the buttocks at the formation position of the absorbing-body deficit portion 22 from the fit embosses 31a as base points.

The above-described intermediate emboss 32 is formed so that the rear end portion of the above-described crotch portion emboss 30 and a part of the front end have an overlapping margin with respect to a direction orthogonal to the above-described virtual line S2. As a result, since rigidity (resistance) of the absorbing body 4 on the double emboss portion of the crotch portion emboss 30 and the intermediate emboss 32 having the overlapping margin in the direction orthogonal to the above-described virtual line S2 increases, the leg pressure from the both sides can be easily converted to the force to raise the region surrounded by the front groove 24 and the rear groove 25 of the Y-shaped groove 23.

The invention claimed is:

1. An absorbent article, comprising
an absorbing body interposed between a permeable front-surface sheet, said front-surface sheet forming a skin contact surface, and an impermeable back-surface sheet, said back-surface sheet forming a skin non-contact surface,
intermittent recess grooves extending in a longitudinal direction in the widthwise central portion of said absorbent article on the skin non-contact surface side of said absorbing body,
a plurality of laterally elongated peripheral embosses formed at intervals in the longitudinal direction of said absorbent article on the skin non-contact surface side on absorbing body areas located peripherally to said recess grooves, and
an absorbing-body deficit portion formed at least between said recess grooves on the skin non-contact surface side.

2. The absorbent article according to claim 1, further comprising an absorbing body middle high portion extending in the longitudinal direction of said absorbent article and raised to the skin contact surface side provided at least on a lateral center part in a longitudinal rear of said absorbent article,
wherein said intermittent recess grooves are formed at said absorbing-body middle high portion,
wherein said plurality of laterally elongated peripheral embosses are located peripherally of said absorbing-body middle high portion,
wherein said absorbing-body deficit portion is a first absorbing-body deficit portion, and
further comprising a second absorbing-body deficit portion, which is formed at least between said recess grooves of the absorbing body at said absorbing-body middle high portion.

3. The absorbent article according to claim 2, wherein
said absorbing-body deficit portion has a rectangular, diamond, wedge or triangular planar cross-section, wherein the planar cross-section is defined by an axis that is parallel to the longitudinal direction of the absorbent article.

4. The absorbent article according to claim 1, further comprising
a first longitudinally extending emboss in a left rear portion and a second longitudinally extending emboss in a right rear portion of said absorbent article on the skin contact surface side of said absorbing body in a region corresponding to the buttocks of a wearer, and
at a position corresponding to said absorbing-body deficit portion, a fit emboss extending to a center part in the width direction of said absorbent article from said rear portion embosses.

5. The absorbent article according to claim 4, wherein
said absorbing-body deficit portion changes shape in the thickness direction of the absorbing body.

6. An absorbent article, comprising
an absorbing body interposed between a permeable front-surface sheet, said front-surface sheet forming a skin contact surface, and an impermeable back-surface sheet, said back-surface sheet forming a skin non-contact surface,
intermittent recess grooves extending in a longitudinal direction of said absorbent article on the skin non-contact surface side of said absorbing body,
a plurality of laterally elongated peripheral embosses formed at intervals in the longitudinal direction of said absorbent article on absorbing body areas located peripherally to said recess grooves,
an absorbing-body deficit portion formed at least between said recess grooves, and
an absorbing body middle high portion extending in the longitudinal direction of said absorbent article and raised to the skin contact surface side provided at least on a lateral center part in a longitudinal rear of said absorbent article, wherein said intermittent recess grooves are formed at said absorbing-body middle high portion, wherein said plurality of laterally elongated peripheral embosses are located peripherally of said absorbing-body middle high portion, wherein said absorbing-body deficit portion is a first absorbing-body deficit portion, and further comprising a second absorbing-body deficit portion, which is formed at least between said recess grooves of the absorbing body at said absorbing-body middle high portion.

7. The absorbent article according to claim 6, wherein said absorbing-body deficit portion has a rectangular, diamond, wedge or triangular planar cross-section, wherein the planar cross-section is defined by an axis that is parallel to the longitudinal direction of the absorbent article.

8. An absorbent article, comprising an absorbing body interposed between a permeable front-surface sheet, said front-surface sheet forming a skin contact surface, and an impermeable back-surface sheet, said back-surface sheet forming a skin non-contact surface, intermittent recess grooves extending in a longitudinal direction of said absorbent article on the skin non-contact surface side of said absorbing body, a plurality of laterally elongated peripheral embosses formed at intervals in the longitudinal direction of said absorbent article on absorbing body areas located peripherally to said recess grooves, an absorbing-body deficit portion formed at least between said recess grooves, a first longitudinally extending emboss in a left rear portion and a second longitudinally extending emboss in a right rear portion of said absorbent article on the skin contact surface side of said absorbing body in a region corresponding to the buttocks of a wearer, and at a position corresponding to said absorbing-body deficit portion, a fit emboss extending to a center part in the width direction of said absorbent article from said rear portion embosses.

9. The absorbent article according to claim 8, wherein said absorbing-body deficit portion changes shape in the thickness direction of the absorbing body.

* * * * *